Jan. 22, 1974 B. J. MACHIN Plant Pat. 3,443
CHRYSANTHEMUM PLANT
Filed Dec. 27, 1971
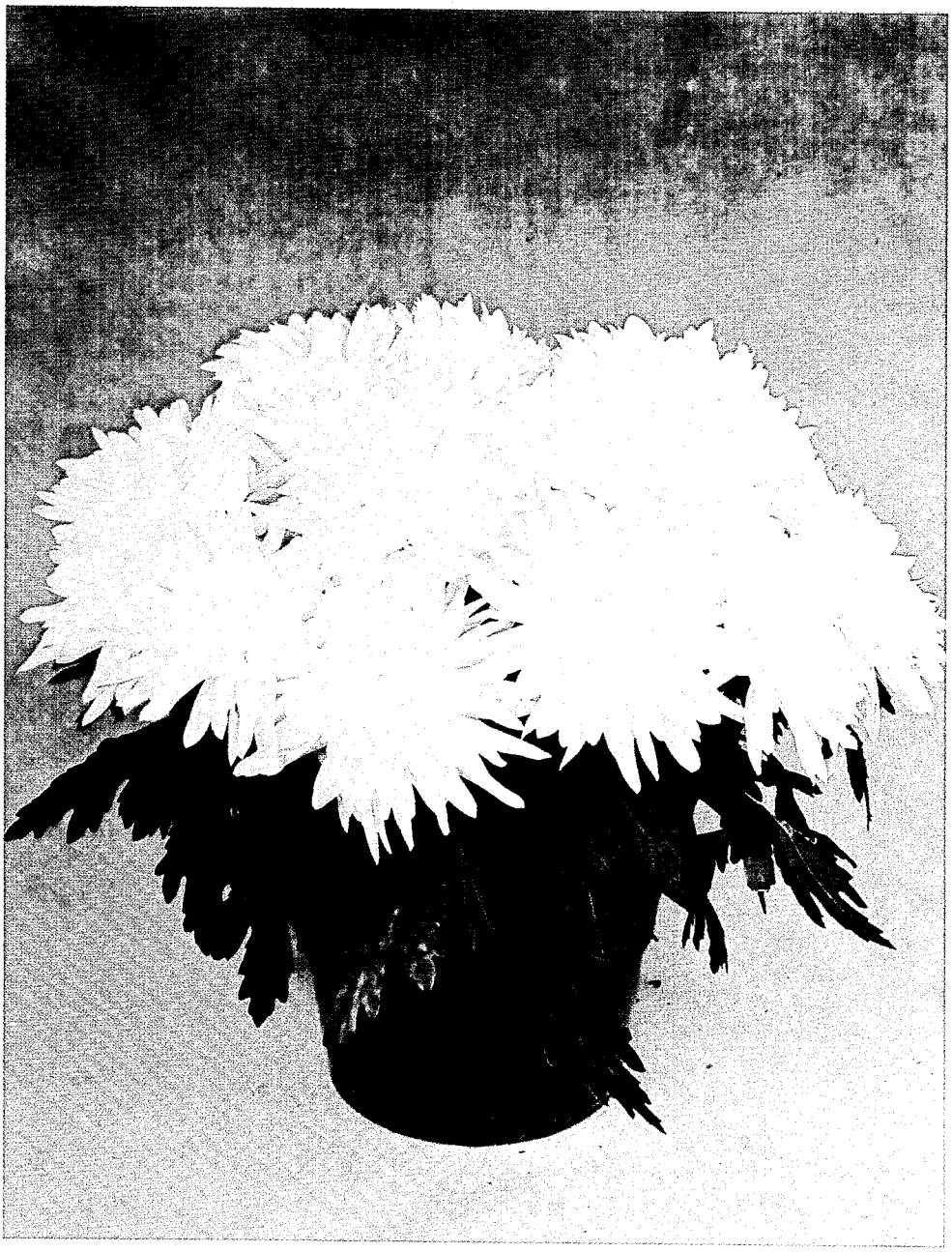

United States Patent Office

Plant Pat. 3,443
Patented Jan. 22, 1974

3,443
CHRYSANTHEMUM PLANT

Barrie John Machin, East Broyle Estate, Chichester, England, assignor to Frampton's Nurseries Limited, Chichester, Sussex, England Filed Dec. 27, 1971, Ser. No. 212,836
Int. Cl. A01h 5/00
U.S. Cl. Plt.—77 1 Claim This invention relates to a new and distinct variety of *Chrysanthemum morifolium* Bailey (pot type) known as Altis.

Altis is a seedling originated by me from a cross made in 1966 between the unpatented variety Bluebell and the unpatented variety Neptune, the former being the seed parent, and the latter being the pollen parent.

The variety Altis resulted from an extensive breeding program with the object of producing an improved white variety for year round pot chrysanthemum production, with more uniformity and reduced flowering time as compared with the existing varieties. Altis has the following improved characteristics over Neptune, its pollen parent.

(1) It is much more responsive and will produce good quality pot plants in 2 weeks less growing time from March to November in Southern England.
(2) It is much easier to control the height of the plant and little or no chemical dwarfing measures are required. Flower color is pure white, as compared with creamy white.
(3) A better breaking action after pinching is obtained and more flowers per plant are formed.

Altis is distinguished from its seed parent Bluebell in the following characteristics:

(1) Flower color is white rather than pink
(2) Flowering response is in 8 weeks rather than 9 weeks
(3) Altis is more prolific in shoot production following a pinch.

The accompanying drawing shows a typical flower of my new variety depicted in color as nearly true as it is reasonably possible to make the same in a color illustration of this character.

Asexual reproduction of this new variety Altis, by rooting vegetative shoots in Sussex, England, shows that the above characteristics are fixed and come true to type through succeeding generations.

The following is a detailed description of the new variety Altis with color terminology in accordance with the Royal Horticultural Society color chart, hereinafter referred to as RHS.

Genus: Chrysanthemum
Species: *Morifolium* Bailey
Type: Pot
Class: Decorative
Breeding: The original seedling resulted from a cross between the variety Bluebell and the variety Neptune, the former being the seed parent, the latter being the pollen parent. The cross was made in 1966 at Frampton's Nurseries Ltd., Forbridge Nursery, Chichester, Sussex, England.
Propagation: Holds its distinguishing characteristics through succeeding propagations by rooting vegetative shoots.
Flower: When grown in Sussex, England, in 3½ inch pots and pinched, up to 8 flowers per plant are formed. When 5 plants are planted per 5 inch pot, 6 flowers are borne on each plant.
Bloom:
*Size.*—Average diameter is 8 cm. when fully open.
*Petalage.*—Decorative with approximately 150 to 200 ray petals and up to ten disc petals.
*Form.*—Decorative.
*Petals.*—Long broad, overlapping, fairly blunt, flat and of medium to thin texture.
Color of open bloom:
Inner face of fully expanded petal, RHS 155D.
Outer face of fully expanded petal, RHS 155D.
Inner face of young petals, RHS 155D.
Outer face of young petal, RHS 155D.
Response Group: 8 weeks.
Temperature tolerance: 55–60° F. at night.
Plant: Wiry and bushy habit at growth.
Foliage:
Medium quality—average internode length 2½ cm.
Medium size.
Color—137D.
Medium texture.
Stem:
Medium thickness and wiry.
Color—146B with reddish tints at flowering.
Water uptake good.

I claim:

1. A new and distinct variety of *Chrysanthemum morifolium* Bailey, substantially as shown and described. characterized particularly as to its novelty by the unique combination of a pure white color, an eight week response time under summer growing conditions, and a relatively large number of flowers per plant.

No references cited.

ROBERT E. BAGWILL, Primary Examiner